United States Patent [19]

Ohtani et al.

[11] Patent Number: 5,718,080

[45] Date of Patent: Feb. 17, 1998

[54] CULTIVATION OF FLOWERING PLANTS

[75] Inventors: Toshio Ohtani; Naoya Fukuda; Sadanori Sase; Limi Okushima, all of Ibaraki, Japan

[73] Assignee: National Research Institute of Agricultural Engineering, Ministry of Agriculture, Forestry and Fisheries, Ibaraki, Japan

[21] Appl. No.: 626,964

[22] Filed: Apr. 3, 1996

[51] Int. Cl.$^6$ ............................................. A01H 3/02
[52] U.S. Cl. .................................... 47/58; 47/DIG. 6
[58] Field of Search ................................ 47/58, DIG. 6

[56] References Cited

U.S. PATENT DOCUMENTS 4,788,793  12/1988  Kadkade ................................. 47/58

FOREIGN PATENT DOCUMENTS 04-349823  1/1991  Japan .

OTHER PUBLICATIONS

Mortensen et al. Effects of light quality on some greenhouse crops. Scientia Horticulturae. vol. 33. pp. 27–36 1987.

McMahon et al. Control of poinsettia growth and pigmentation by manipulating light quality. Hortscience. vol. 25. p. 1068. (Abstract #32) 1990.

McMahon et al. Growth of Dendranthema x grandiflorum (Ramat.) Kitamura under various spectral filters. Journal of the American Society for Horticultural Science. vol. 116. pp. 950–954 1991.

Karlsson et al. Light quality initiating for ending the day affects internode length in Petunia. Hortscience. vol. 30. p. 861. (Abstract #727) 1995.

Scientia Horticulturae, vol. 48, pp. 141–151, 1991, Roar MOE, et al., "Stem Elongation and Flowering of the Long–Day Plant Campanula Isophylla Moretti in Response to Day and Night Temperature Alternations and Light Qualtiy".

Scientia Horticulturae, vol. 45, pp. 345–351, 1991, M. Appelgren, "Effects of Light Quality on Stem Elongation of Pelargonium In Vitro".

J. Amer. Soc. Hort. Sci., vol. 117, No. 3, pp. 481–485, 1992, Nihal C. Rajapakse, et al., "Regulation of Chrysanthemum Growth by Spectral Filters".

De Graaf et al, The Effect of Day Extensions with Different Light Qualities on the Morphogenesis of Fuchsia, Petunia and Pelargonium, Acta Horticulurae, vol. 305, 1992, pp. 85–94.

*Primary Examiner*—Douglas W. Robinson
*Assistant Examiner*—Melissa L. Kimball
*Attorney, Agent, or Firm*—Oblon, Spivak, McClelland, Maier & Neustadt, P.C.

[57] ABSTRACT

To make it possible to control the forms of flowering plants by controlling light quality of cultivation light, without using any chemicals such as dwarfing agents, a method of cultivating a flowering plant selected from the group consisting of the genus Petunia, the genus Pelargonium and the genus Euphorbia is proposed, which comprises controlling light quality of cultivation light in the daylight period after a seedling culture stage, in particular, after true-leaf development until blooming or bract formation to thereby control the forms concerning the height of a plant, the length of a branch, the length of a corolla, the length of a flower tube, the number of florets, the dimensions of a flower cluster, the number of bracts or the length of a bract.

10 Claims, 5 Drawing Sheets

CULTIVATION OF FLOWERING PLANTS

BACKGROUND OF THE INVENTION

1. Field of the Invention

This invention relates to a method of cultivating flowering plants. More particularly, this invention relates to a method of cultivating flowering plants that controls the forms of plant organisms by controlling light quality of cultivating light, to enable, e.g., dwarfing to make small the height of a plant.

2. Description of the Related Art

In recent years, there is an increasing demand for flowering plants cultivated in pots so that they can be admired on tables. With regard to flowering plants in such pot cultivation, it is commonly desired to make their plant organisms small in size. For this purpose, in the pot cultivation, the plant organisms are made small usually by a method in which a dwarfing agent such as uniconazole is sprayed on the surfaces of leaves. The DIF method is also employed, which utilizes differences in temperature between night and day.

The use of dwarfing agents, however, causes anxiety about bad influence on the human body and environment. Accordingly, it is sought to dwarf flowering plants in the pot cultivation without using dwarfing agents.

Meanwhile, when flowering plants are cultivated in pots, it is also sought to enable control of the number and size of flowers, the density of florets that constitute a flower cluster, and the number and size of bracts.

As one of the methods for the dwarfing and other morphological control of flowering plants, it is intended to control light quality of cultivation light, which is so attempted in recent years in order to control the growth of fruits and vegetables or green vegetables. However, how the light quality affects plants is in a great variety depending on not only various factors such as wavelength distribution of the light, light intensity and irradiation time but also the type of plants. Hence, it is not easy to find out cultivation conditions under which any desired types of plant organisms are dwarfed to have the desired forms suitable for the pot cultivation. Thus, under existing circumstances, no dwarfing cultivation is carried out by light quality control also in respect of flowering plants such as petunias, geraniums and poinsettias.

SUMMARY OF THE INVENTION

The present invention intends to solve such problems involved in the prior art. An object of the present invention is to make it possible to control the forms of flowering plants by controlling light quality of cultivation light, without using any chemicals such as dwarfing agents.

The present inventors have discovered that the above object can be achieved by controlling light quality of cultivation light after a seedling culture stage, in respect of the genus Petunia, the genus Pelargonium and the genus Euphorbia. Thus, they have accomplished the present invention.

More specifically, the present invention provides a method of cultivating a flowering plant selected from the group consisting of the genus Petunia, the genus Pelargonium and the genus Euphorbia, the method comprising controlling light quality of cultivation light in the daylight period after a seedling culture stage, in particular, after true-leaf development until blooming or bract formation to thereby control the forms concerning the height of a plant,
 the length of a branch, the length of a corolla, the length of a flower tube, the number of florets, the dimensions of a flower cluster, the number of bracts or the length of a bract.

As particularly preferred embodiments, the present invention provides, in the cultivation of the flowering plant belonging to the genus Petunia, a method wherein non-white light, particularly preferably yellow light, is used as the cultivation light to thereby dwarf the height of the plant, or a method wherein green light is used as the cultivation light to thereby make the length of the flower tube greater.

The present invention also provides, in the cultivation of the flowering plant belonging to the genus Pelargonium, a method wherein non-white light, particularly preferably yellow light or blue light, is used as the cultivation light to thereby dwarf the height of the plant, or a method wherein red light or blue light is used as the cultivation light to thereby dwarf the height of the plant and at the same time increase the density of florets.

The present invention still also provides, in the cultivation of the flowering plant belonging to the genus Euphorbia, a method wherein blue light is used as the cultivation light to thereby dwarf the height of the plant, or a method wherein yellow light is used as the cultivation light to thereby increasing the number of bracts and at the same time make the length of a bract greater.

DETAILED DESCRIPTION OF THE INVENTION

Of the flowering plants to be cultivated in the present invention, those of the genus Petunia include a petunia (*Petunia hybrida* Vilm.); the genus Pelargonium, a geranium (*Pelargonium zonale, Pelargonium inquinans, Pelargonium hortorum*, including hybrids thereof), a pelargonium (*Pelargonium cucullatum, Pelargonium grandiflorum, Pelargonium angulosum, Pelargonium domesticum*, including hybrids thereof), an Ivy geranium (*Pelargonium peltatum, Pelargonium lateripes*, including hybrids thereof) and a scented leaved geranium (*Pelargonium graveolens, Pelargonium radula, Pelargonium odoratissimum, Pelargonium quercifolium*, including hybrids thereof); and the genus Euphorbia, a poinsettia (*Euphorbia pulcherrima* Willd.) and a euphorbia (*Euphorbia marginata* Pursh).

Figure 1:
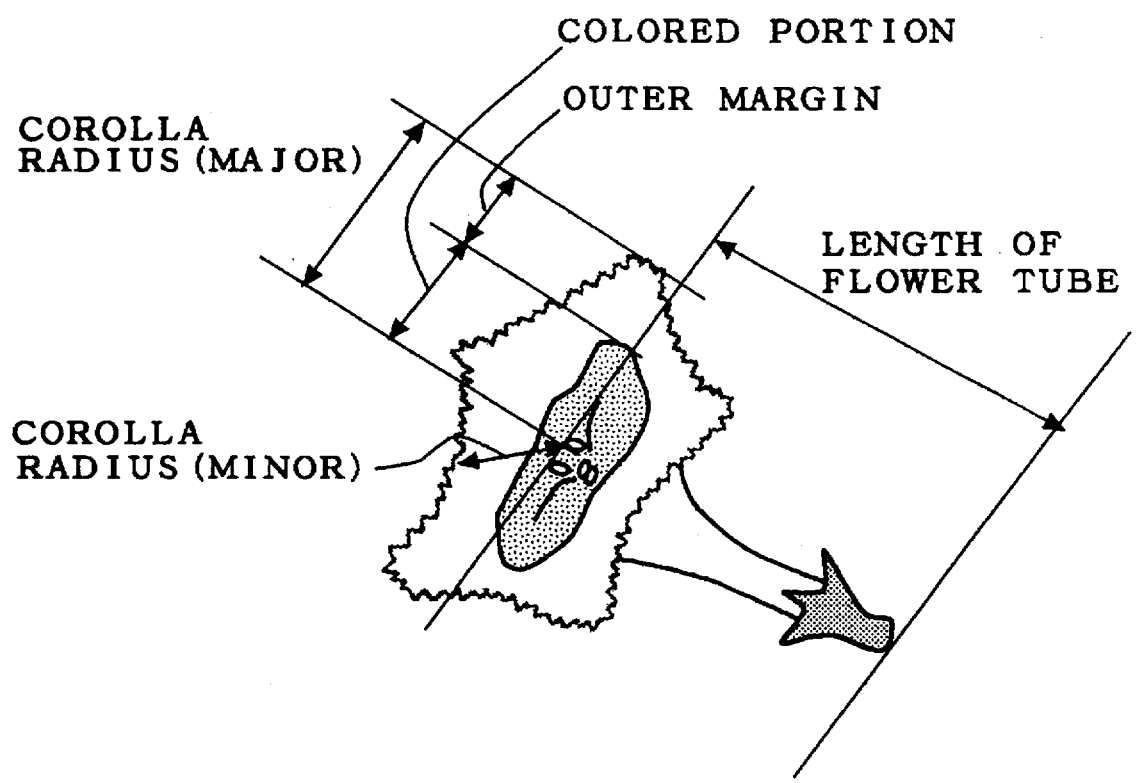
FIG. 1 is a view to illustrate the terms relating to the form of flower of a petunia.
Figure 2:
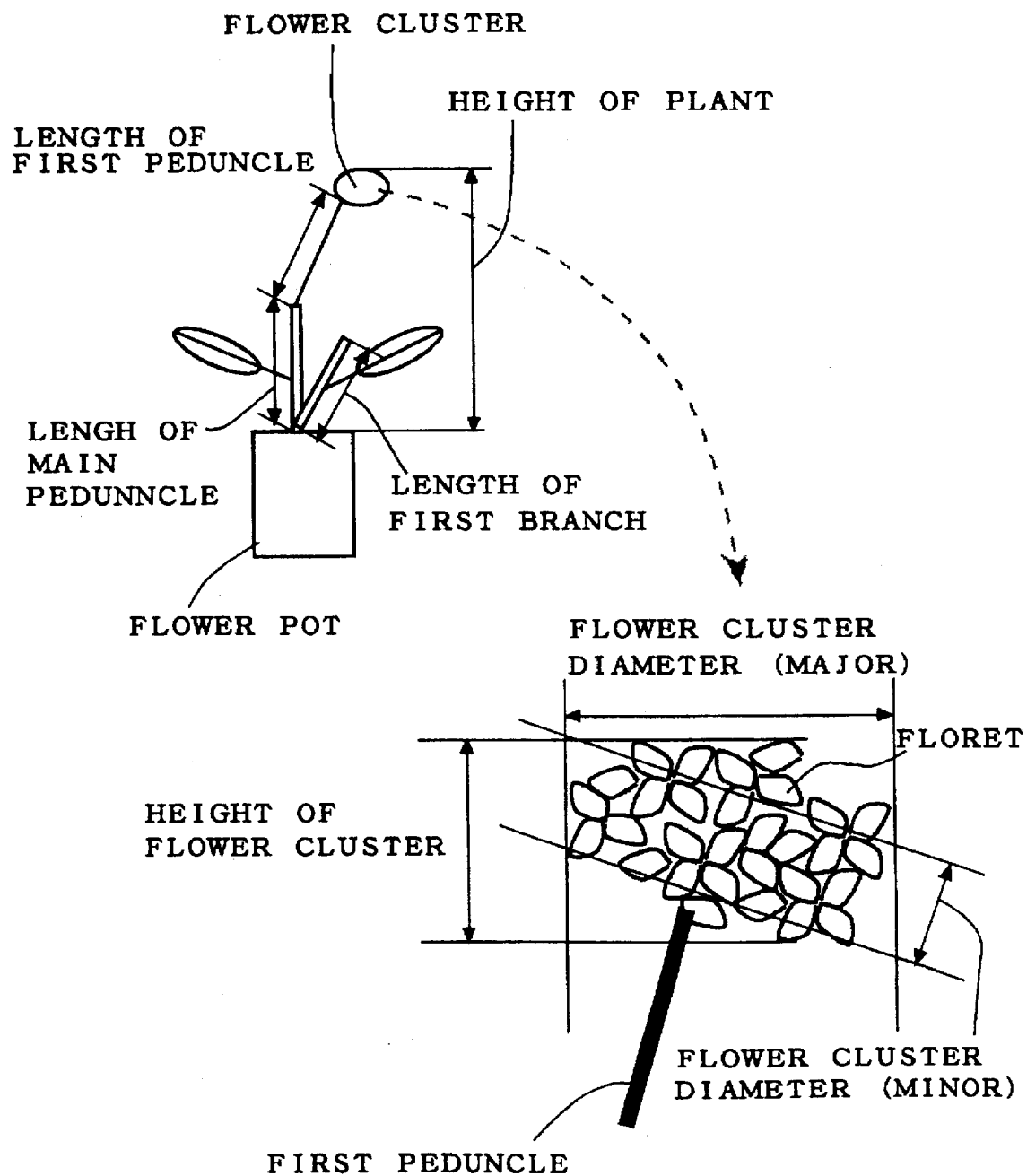
FIG. 2 is a view to illustrate the terms relating to the form of flower of a geranium.

In the present invention, among the terms relating to the form of flower of petunias, the portions respectively meant by "length of flower tube", "outer margin", "colored portion", "corolla radius (major)" and "corolla radius (minor)" are as shown in FIG. 1 in respect of a petunia. Among the terms relating to the form of flowering plant of the genus Pelargonium, the portions respectively meant by "flower cluster", "floret", "flower cluster diameter (major)", "flower cluster diameter (minor)", "height of flower cluster", "height of plant", "length of first peduncle", "length of main peduncle" and "length of first branch" are as shown in FIG. 2 in respect of a geranium.

In the cultivation method of the present invention, the light quality of cultivation light, stated more specifically, the wavelength distribution of cultivation light, used when these plants are cultivated is controlled to thereby attain dwarfing or other intended morphological control.

Here, as manners for controlling the wavelength distribution of cultivation light, it is meant to use light of the wavelength region assorted for each color such as white color, red color, yellow color, green color or blue color. The wavelength distribution of cultivation light of each color, however, is by no means so strict as to exclude the light of the wavelength regions of different colors. The present invention can be effective so long as the middle of energy distribution of cultivation light is within the region of each color. For example, five kinds of light quality as shown in Table 1 can be obtained when metal halide lamps of respective colors are used as light sources. In the present invention, the light quality of cultivation light can be controlled using the light assorted in this way.

plants, the intensity of light and the length of a day. Such cultivation may be carried out after a seedling culture stage, and irradiation with the light having specific light quality need not be made in a seed stage or germinal stage. Also, it is unnecessary to continue irradiation with the light having specific light quality, after plants have well grown and have bloomed, or after bracts have well grown. For example, when plant organisms are dwarfed, the light with specific light quality is used as the cultivation light in the cultivation period of from true-leaf development until blooming or bract formation.

The time for which the flowering plants are irradiated with the cultivation light a day during the cultivation may be the same as that in conventional cultivation methods. It is unnecessary to make the irradiation all day. The irradiation time may be appropriately determined in accordance with the desired flowering period, the desired bract formation time and so forth. Thus, for example, with regard to short-day plants such as poinsettias, the dark period may preferably be made longer than the light period when the cultivation comes to the latter period.

TABLE 1

| | Wavelength Distribution of Cultivation Light (percentages to total amount of light) | | | | | | |
|---|---|---|---|---|---|---|---|
| Wavelength (nm): | UV-A 300–400 | Blue 400–500 | Green 500–550 | Yellow 550–600 | Red 600–700 | Near infrared 700–750 | Infrared >750 |
| Light quality of cultivation light: | | | | | | | |
| White light: | 2.25 | 9.67 | 5.69 | 10.41 | 15.31 | 10.00 | 48.35 |
| Red light: | 1.80 | 6.77 | 2.68 | 21.41 | 32.62 | 4.60 | 31.35 |
| Yellow light: | 0.35 | 3.17 | 0.36 | 47.06 | 5.85 | 1.11 | 42.34 |
| Green light: | 7.43 | 9.07 | 33.95 | 5.49 | 6.68 | 3.70 | 34.22 |
| Blue light: | 6.15 | 40.88 | 5.84 | 6.68 | 5.18 | 3.62 | 34.13 |

What cultivation light be used among the groups of cultivation light with such light quality may be appropriately determined in accordance with the varieties of flowering plants to be cultivated or the desired forms to be imparted to the plant organisms of the flowering plants.

For example, when the height of a plant of a flowering plant belonging to the genus Petunia is dwarfed, non-white light is used. In this case, it is particularly preferable to use yellow light. When the length of a flower tube of the flowering plant belonging to the genus Petunia is made greater, green light is used.

Also when the height of a plant of a flowering plant belonging to the genus Pelargonium is dwarfed, non-white light is used. In this case, it is particularly preferable to use yellow light or blue light. When the height of a plant of the flowering plant belonging to the genus Pelargonium is dwarfed and at the same time the density of florets is increased, red light or blue light is used.

When the height of a plant of a flowering plant belonging to the genus Euphorbia is dwarfed, blue light is used. When the number of bracts of the flowering plant belonging to the genus Euphorbia and at the same time the length of a bract is made greater, yellow light is used.

In the present invention, the time to start the cultivation under light having the specific light quality as shown above, and the period for such cultivation may be appropriately determined in accordance with the varieties of the flowering plants, the desired forms to be imparted to the flowering In the present invention, the same procedure as in conventional cultivation methods may be used except for the control of light quality of cultivation light.

EXAMPLES

The present invention will be described below in greater detail by giving Examples.

Example 1

Cultivation of Petunias

Seedling-cultured petunias (name of variety: baccarat blue picotee; colored portions of corollas: blue; outer margins: white) were cultivated in the following way over a period of 6 weeks from August 18th and on five plants per cultivation light with different kind of light quality.

More specifically, the seedling-cultured petunias were transplanted to plastic bottles, which were then set on the bottoms of growth chambers. At the upper part in each growth chamber, a metal halide lamp was provided as a light source and its ultraviolet rays were shielded by an acrylic plate. Light sources with five kinds of light quality as previously shown in Table 1 were used as cultivation light sources. In this instance, the height of each light source was adjusted so that the light intensity of cultivation light was 400 $\mu mol.m^{-2}.s^{-1}$ at the top of the plant. The length of a day was divided into 12 hours for the light and dark periods each.

During the cultivation, the height of plant, living weight, dry weight, and flower's dimensions [corolla radius (major), corolla radius (minor), length of flower tube, and breadth of outer margin] were measured at intervals of a week.

The results of measurement are shown in Table 2 in respect of the height of plant on the 42nd day after the cultivation in growth chambers, and in Table 3 in respect of the dimensions of flowers on the 30th day after the cultivation in growth chambers. In Table 2, the alphabetic letter symbols show that there are significant differences at a level of 5% according to the Duncan's multiple test, between values marked with different letters among the group of a, ab, abc and b.

As is seen from Table 2, the height of plant can be held down when cultivated under non-white light, to obtain dwarfed plant organisms, and especially when cultivated under yellow light the height of plant can be dwarfed by about 70% compared with the case when cultivated under white light; thus, this method is effective for the dwarfing of plant organisms.

In this instance, there was no difference in the total dry weight of leaves, flowers, stems and roots between those cultivated under yellow light and those cultivated under other light. Thus, it can be confirmed that the plants were in normal growth.

With regard to the dimensions of flowers, as is seen from Table 3, the corolla radius can be made smaller when cultivated under yellow light and can be made greater when cultivated under blue light. As is also seen therefrom, the length of flower tube can be made greater when cultivated under green light.

Example 2

Cultivation of Geraniums

Seedling-cultured geraniums (name of variety: Orbic white) were cultivated over a period of from April 6th to the end of June and on five plants per cultivation light with different kind of light quality, using the same growth chambers as in Example 1 except that the light intensity of cultivation light was adjusted so as to be 360 $\mu mol.m^{-2}.s^{-1}$ at the top of the plant. The length of a day was divided into 12 hours for the light and dark periods each.

During the cultivation, the height of plant, length of first peduncle, length of main peduncle, length of first branch, number of florets of first flower cluster, and dimensions of flower cluster [flower cluster diameter (major), flower cluster diameter (minor), and height of flower cluster] were measured at intervals of a week.

Figure 3:
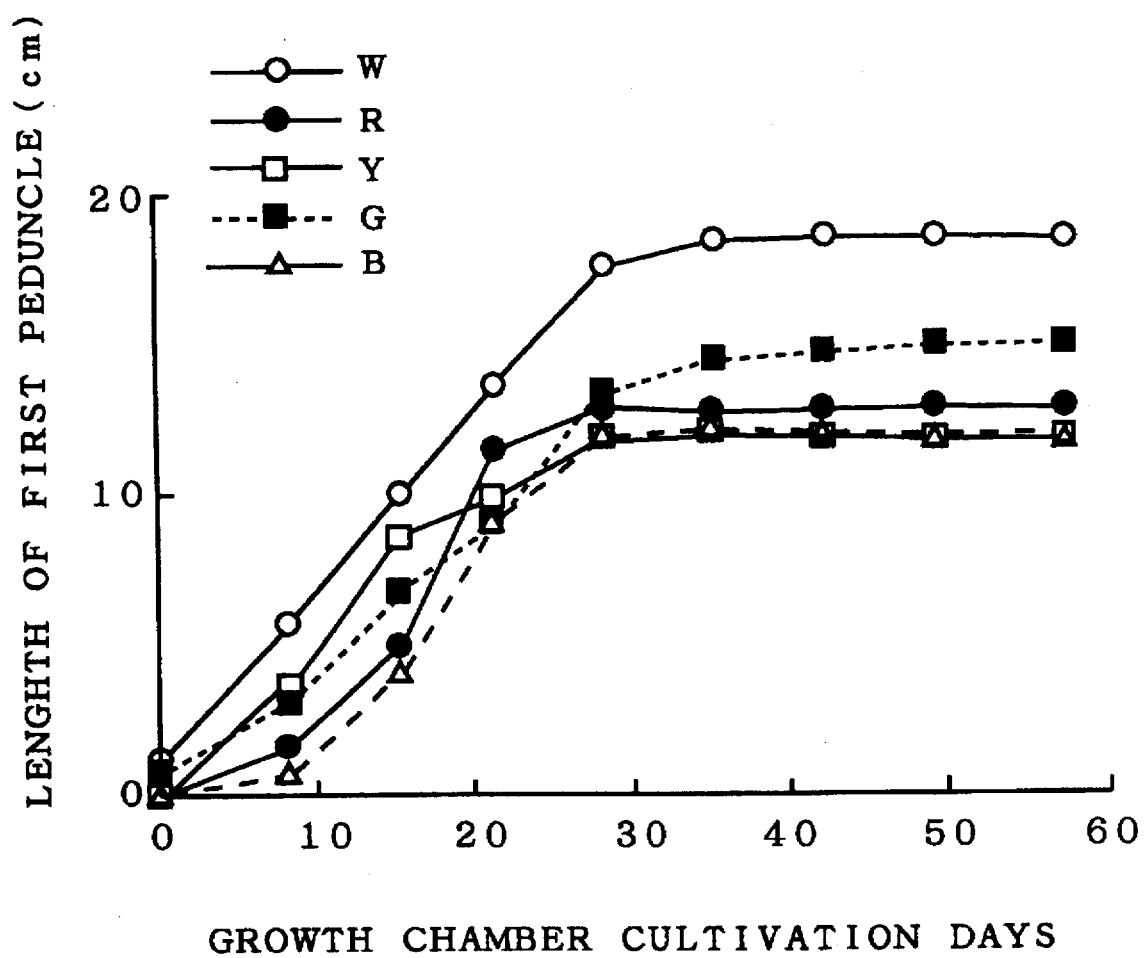
FIG. 3 shows the relationship between the length of the first peduncle of a geranium and the number of cultivation days.

The results of measurement are shown in Table 2 in respect of the height of plant on the 56th day after the cultivation in growth chambers. The results on the length of first peduncle are shown in FIG. 3. The results on the number of florets and dimensions of flower cluster at the time when the number of florets per flower cluster was maximum are shown in Table 4.

As is seen from Table 2, the height of plant can be held down when cultivated under non-white light, to obtain dwarfed plant organisms, and especially when cultivated under yellow light or blue light the height of plant can be dwarfed by about 70% compared with the case when cultivated under white light; thus, this method is effective for the dwarfing of plant organisms.

As is seen from FIG. 3, dwarfed plant organisms having short first peduncles can be obtained when cultivated under non-white light, and especially when cultivated under yellow light or blue light the length of first peduncle can be dwarfed by about 65% compared with the case when cultivated under white light; thus, this method is effective for the dwarfing of plant organisms. Similar tendencies of dwarfing are also observed in respect of the length of main peduncle and length of first branch. Thus, the control of light quality is seen to be effective for the dwarfing of the whole plant organism.

As is seen from Table 4, the number of florets of the first flower cluster can be increased when cultivated under white light, red light or yellow light, and also the dimensions of flowers can be made smaller when cultivated under red light or blue light. Thus, compact flower clusters having a high floret density are seen to be obtainable when cultivated under red light or blue light.

Example 3

Cultivation of Poinsettias

Poinsettias (name of variety: V10) were seedling-cultured from the first of September until the first of October. Thereafter, the seedling-cultured poinsettias were cultivated over a period of three months and on five plants per cultivation light with different kind of light quality, using the same growth chambers as in Example 1 except that the light intensity of cultivation light was adjusted so as to be 600 $\mu mol.m^{-2}.s^{-1}$ at the top of the plant. The length of a day was divided into 12 hours for the light and dark periods each at the initial stage, but changed to a short-day condition of 10 hours for the light period and 14 hours for the dark period at the latter stage of the growth stage (after elapse of one month after the start of the cultivation in growth chambers).

During the cultivation, the height of plant, number of bracts, and maximum length of bract were measured at intervals of a week.

Figure 4:
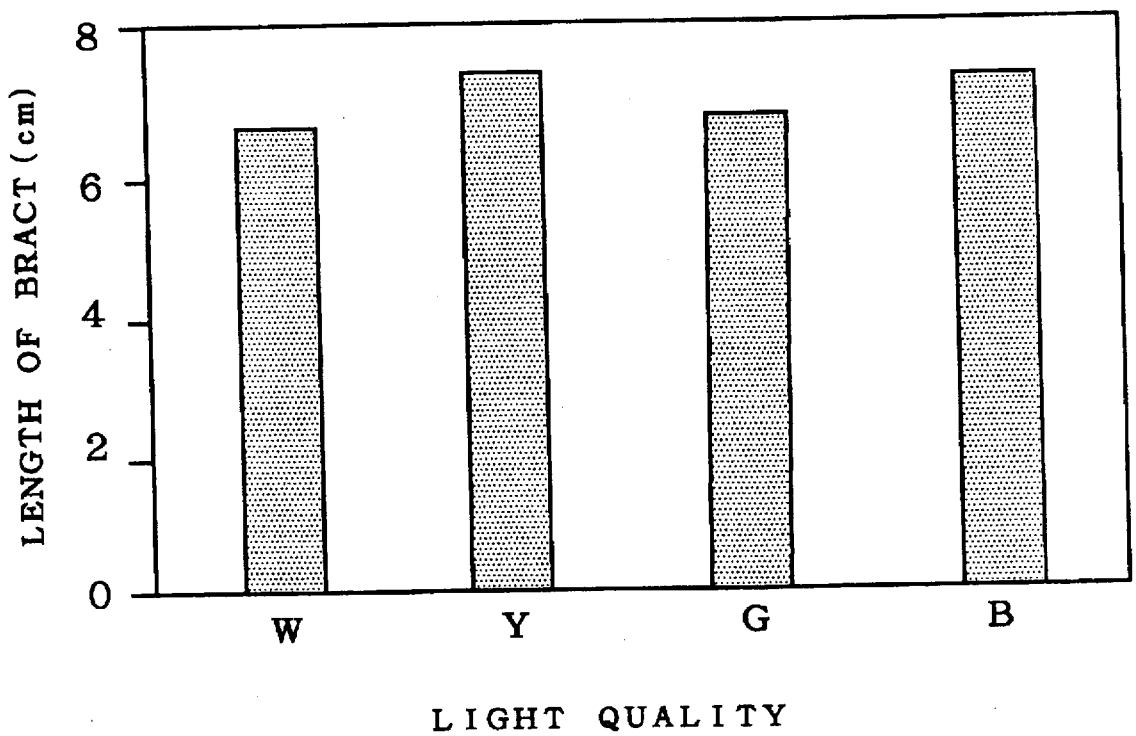
FIG. 4 shows the relationship between the length of a bract of a poinsettia and the light quality.
Figure 5:
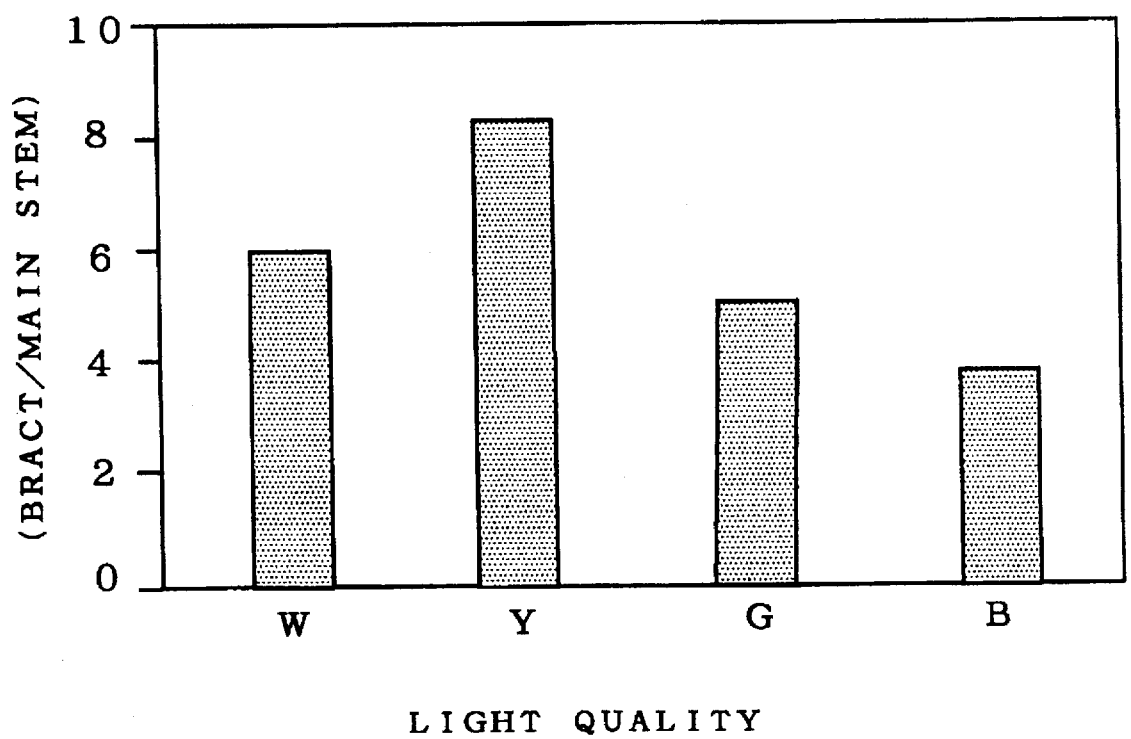
FIG. 5 shows the relationship between the number of bracts of a poinsettia and the light quality.

The results of measurement are shown in Table 2 in respect of the height of plant on the 100th day after the cultivation in growth chambers. The results on the maximum length of bract on the 100th day after the cultivation in growth chambers are shown in FIG. 4. The results on the number of bracts are shown in FIG. 5 as the number of bracts per the main stem.

As is seen from Table 2, the height of plant can be held down when cultivated under blue light, to obtain dwarfed plant organisms.

As is also seen therefrom, the height of plant can be made greater when cultivated under yellow light. As is also seen from FIGS. 4 and 5, the number of bracts can be increased and the maximum length of bract can be made greater when cultivated under yellow light.

TABLE 2

| Light quality | Height of Plant (cm) | | |
|---|---|---|---|
| | Plants tested | | |
| | Geranium | Petunia | Poinsettia |
| White: | 17.1 b | 15.9 b | 39.1 bc |
| Red: | 15.9 b | 13.6 ab | 38.5 abc |
| Yellow: | 12.2 a | 11.1 a | 41.4 c |
| Green: | 14.7 ab | 14.8 b | 37.5 ab |
| Blue: | 12.4 a | 14.4 b | 35.8 a |

TABLE 3

Dimensions of Flowers of Petunia (average values; cm)

| Light quality | Length of flower tube | Breadth of outer margin | Corolla radius (major) | Corolla radius (minor) |
|---|---|---|---|---|
| Blue: | 4.71 | 0.85 | 3.05 | 1.83 |
| Yellow: | 4.88 | 1.49 | 2.84 | 1.68 |
| Red: | 5.29 | 1.04 | 3.13 | 1.79 |
| Green: | 5.64 | 0.95 | 3.11 | 1.66 |
| White: | 5.13 | 1.08 | 3.03 | 1.74 |

TABLE 4

Geranium Flower Clusters and Florets

| Light quality | Number of florets (f/c)* | Flower cluster diameter (major) (cm) | Flower cluster diameter (minor) (cm) | Height of flower cluster (cm) |
|---|---|---|---|---|
| White: | 17.3 | 10.13 | 8.40 | 7.63 |
| Red: | 18.5 | 8.45 | 6.58 | 6.53 |
| Yellow: | 15.5 | 9.27 | 7.67 | 7.67 |
| Green: | 9.5 | 8.63 | 7.27 | 6.97 |
| Blue: | 13.5 | 8.73 | 6.55 | 6.18 |

*(florets per flower cluster)

As described above, the present invention makes it possible to carry out the dwarfing and other morphological control of flowering plants such as petunias, geraniums and poinsettias, without using any chemicals such as dwarfing agents.

What is claimed is:

1. A method of cultivating a flowering plant belonging to the genus Petunia, which comprises cultivating the plant in the daylight period after a seedling culture stage under green light to increase the length of the flower tube thereof.

2. The method of claim 1, wherein said Petunia plant is a *Petunia hybrida*.

3. The method of claim 1, wherein a middle portion of energy distribution of said green light is within a wavelength range of 500 to 550 nm.

4. The method of claim 3, wherein said middle portion comprises 33.95% of a total amount of said green light.

5. The method of claim 1, wherein said green light has an intensity of 400 μmol. $m^{-2}.s^{-1}$ at the top of said plant.

6. A method of cultivating a flowering plant belonging to the genus Pelargonium, which comprises cultivating the plant in the daylight period after a seedling culture stage under red light in order to increase the density of florets thereof.

7. The method of claim 6, wherein said plant of the genus Pelargonium is selected from the group consisting of *Pelargonium zonale, Pelargonium inquinans, Pelargonium hortorum, Pelargonium cucullatum, Pelargonium grandiflorum, Pelargonium angulosum, Pelargonium domesticum, Pelargonium peltatum, Pelargonium lateripes, Pelargonium graveolens, Pelargonium radula, Pelargonium odoratissimum,* and *Pelargonium quercifolium* and hybrids thereof.

8. The method of claim 6, wherein a middle portion of energy distribution of said red light is within a wavelength range of 600 to 700 nm.

9. The method of claim 8, wherein said middle portion comprises 32.62% of a total amount of said red light.

10. The method of claim 6, wherein said red light has an intensity of 360 μmol.$m^{-2}.s^{-1}$ at the top of said plant.

* * * * *